United States Patent [19]

Jonas

[11] 4,169,845
[45] Oct. 2, 1979

[54] METHOD OF PREPARING TRANSITION METAL-OLEFIN COMPLEX COMPOUNDS AND ALKALI METAL-TRANSITION METAL-OLEFIN COMPLEX COMPOUNDS

[75] Inventor: Klaus Jonas, Mülheim, Fed. Rep. of Germany

[73] Assignee: Studiengessellschaft Kohle mbH, Mülheim, Fed. Rep. of Germany

[21] Appl. No.: 851,558

[22] Filed: Nov. 14, 1977

[30] Foreign Application Priority Data

May 27, 1977 [DE] Fed. Rep. of Germany ....... 2724111

[51] Int. Cl.$^2$ .......................... C07F 7/00; C07F 7/28; C07F 11/00; C07F 15/00
[52] U.S. Cl. ..................... 260/429 CY; 260/346.11; 260/429.5; 260/438.5 R; 260/439 CY
[58] Field of Search ................. 260/439 CY, 429 CY, 260/438.5 R, 429.5, 346.1 M

[56] References Cited

PUBLICATIONS

Brown et al., The J. of Organic Chem., V 35, pp. 1191–1193 (1970).
Trifan et al., J.A.C.S., 79, pp. 2746–2747 (1957).
Jonas et al., Angew. Chem. Int. Ed. Engl., V 15, pp. 767–768 (1976).
Bönnemann et al., Angew. Chem. Int. Ed. Engl., V 15, pp. 46–49 (1976).
Fischer et al., Angew. Chem. Int. Ed., V 12, pp. 565–566 (1973).
Jonas, Angew. Chem. Int. Ed., V 14, pp. 752–753 (1975).
Fritz et al., Chem. Ber. 97 1829–1833 (1964).

*Primary Examiner*—Helen M. S. Sneed
*Attorney, Agent, or Firm*—Sprung, Felfe, Horn, Lynch & Kramer

[57] ABSTRACT

The invention relates to the reaction of cyclopentadienyl-transition metal compounds, $(C_5H_5)_2M$ or $C_5H_5$—$M(L)_n$ (M=transition metal, L=olefin), with alkali metal in the presence of olefins, with detachment of the $C_5H_5$ rings from the transition metal atom to form alkali metal cyclopentadienide, leads, to transition metal-olefin complex compounds free of alkali metal or also containing alkali metal, in yields of greater than 65%, the latter compounds being able to contain one or even several alkali metal atoms per transition metal atom.

It is moreover possible, depending on the selection of the stoichiometry or of the reaction compounds, and depending on the nature of the transition metal, to detach only one or also both cyclopentadienyl rings from the transition metal atom, so that by this method the most various transition metal-olefin complex compounds can be prepared, namely transition metal-olefin complex compounds containing $C_5H_5$ or alkali metal-transition metal-olefin complex compounds free of $C_5H_5$.

4 Claims, No Drawings

METHOD OF PREPARING TRANSITION METAL-OLEFIN COMPLEX COMPOUNDS AND ALKALI METAL-TRANSITION METAL-OLEFIN COMPLEX COMPOUNDS

BACKGROUND

A number of methods are known for the preparation of CO- and NO-free olefin complex compounds of the transition metals. The method developed by Wilke et al., whereby transition metal salts are reduced by means of organometallic compounds of metals of Groups I to III of the Periodic Table, especially aluminum, has found the widest application. As described in German Pat. No. 1,191,375, nickel(II) acetylacetonate reacts with monoethoxydiethyl aluminum in the presence of cyclooctadiene(1,5) to form bis-(cyclooctadiene)-nickel(O), $(C_8H_{12})_2Ni(O)$. If, instead of cyclooctadiene, all-trans-cyclododecatriene is added, a cyclododecatriene-nickel(O), $C_{12}H_{18}Ni(O)$ is formed, or if a cyclooctatetraene is added, a cyclooctatetraene-nickel(O), $(C_8H_8Ni)_2$, is formed.

Furthermore, it is possible to obtain such transition metal compounds by electrochemical reduction (German Offenlegungsschrift No. 2007076). The method of the co-condensation of transition metal atoms and olefins, which requires relatively extensive apparatus, also produces such complex compounds (Angew. Chem. 87, p 217, 1975). Nevertheless, they are obtainable by this method in no more than a moderate yield.

All of the above-named and hitherto known methods lead to transition metal-olefin complex compounds in which the lowest oxidation number of the transition metal atom amounts to zero.

THE INVENTION

It has now been found, and it has already been briefly reported in a first advance report concerning two cobalt and two nickel complex compounds (Angew. Chem. 88 p. 808, 1976), that the reaction of cyclopentadienyl-transition metal compounds, $(C_5H_5)_2M$ or $C_5H_5-M(L)_n$ (M=transition metal, L=olefin), with alkali metal in the presence of olefins, with detachment of the $C_5H_5$ rings from the transition metal atom to form alkali metal cyclopentadienide, leads, even at low temperature (about $-60°$ C.) to transition metal-olefin complex compounds free of alkali metal or also containing alkali metal, in yields of greater than 65%, the latter compounds being able to contain one or even several alkali metal atoms per transition metal atom.

It is moreover possible, depending on the selection of the stoichiometry or of the reaction compounds, and depending on the nature of the transition metal, to detach only one or also both cyclopentadienyl rings from the transition metal atom, so that by this method the most various transition metal-olefin complex compounds can be prepared, namely transition metal-olefin complex compounds containing $C_5H_5$ and free of $C_5H_5$ or alkali metal-transition metal-olefin complex compounds containing $C_5H_5$ and free of $C_5H_5$.

The preferred alkali metals are lithium, sodium or potassium, and the transition metals are principally the metals of Group VIII, but also metals such as chromium, molybdenum, vanadium and titanium. For the olefins bound to the transition metal atom, monoolefins such as bicycloheptene, or polyolefins such as cyclooctadiene or cyclododecatriene, as well as acyclic monoolefins such as ethylene, have proven especially desirable, while the donors complexed to the alkali metal atom are ethers, such as dialkyl ethers, each alkyl group having two to six carbon atoms, specifically linear alkyls, or diaryl ethers, for example monocyclic or dicyclic carbocyclic diaryl ethers, such as diphenyl ether, ditolyl ether etc., tetrahydrofuran, dioxane, polyethers such as monoglymes, diglymes etc., as well as simple, cyclic or chelatizing tertiary amines such as trialkyl amines having two to six carbon atoms in each alkyl group, trimethyl amine, morpholine or tetramethylene diamine.

The preparation of the complex compound is performed by mixing or saturating with the olefin, the cyclopentadienyl-transition metal compounds dissolved or suspended in appropriate inert solvents under inert gas, and adding to this mixture the alkali metal in the form of finely divided sand or also in the form of larger metal pieces. The reaction heat that might be produced is removed by cooling. After the reaction has ended, the complex compounds are separated from the insoluble by-products (excess alkali metal and alkali metal cyclopentadienide), and the product of the invention is isolated from the filtrate by crystallization. Appropriate solvents for such reactions have proven to be ethers, preferably tetrahydrofuran, or also dimethoxyethane, diglymes etc., with or without the addition of tertiary amines, but also aliphatic hydrocarbons such as pentane, hexane, heptane, cyclopentane or cyclohexane as well as carbocyclic (preferably monocyclic carbocyclic) aromatic hydrocarbons, such as benzene or toluene. The reaction temperatures to be used in each case will depend on the nature of the complex compound being prepared. Temperatures between about $-60°$ C. and about $+100°$ C. are usable, especially the range about $-60°$ C. and room (ambient—about 20° C.) temperature.

The special advantage of the method of the invention lies in the fact that, on the one hand, alkali metal-transition metal-olefin complex compounds can be prepared under very mild conditions of temperature and pressure, products which are not obtainable by any of the methods known or described hitherto. Also, alkali metal-free transition metal-olefin complex compounds can be prepared in a simple manner by this method. For example, $C_5H_5CoCOD$ is obtained directly from $(C_5H_5)_2Co$ and lithium in the presence of cyclooctadiene(1,5) (COD), even at 0° C., a method which has never previously been described.

The transition metal complex compounds or their solutions obtained by the method of the invention can be used as catalysts for the oligomerization and polymerization of diolefins. The alkali metal-containing complex compounds are especially suitable as selective reducing agents.

EXAMPLES

EXAMPLE 1

6.5 g of $(C_5H_5)_2Ni$ and 15 ml of cyclooctadiene(1,5) ($C_8H_{12}$=COD) are stirred under argon in 45 ml of tetrahydrofuran (THF) with 485 mg of lithium sand for four hours at 0° C. Bis-(cyclooctadiene-nickel(O) ((COD)$_2$Ni) precipitates, which is filtered off and recrystallized from toluene.

Yield: 7.5 g = 80% of the $(C_5H_5)_2Ni$ put in.

Calculated: Ni, 21.3%. Found: Ni, 21.0%.

EXAMPLE 2

40 g of the $(COD)_2Ni$ prepared in accordance with Example 1 with an equivalent amount of lithium with respect to $(C_5H_5)_2Ni$, is then stirred in 750 ml of THF with 5 g of lithium sand for about 2 hours at 0° C. The $(COD)_2Ni$ has then gone completely into solution. The now dark red reaction solution is separated from excess lithium by filtration and an equal amount of diethyl ether is added. At $-30°$ C. $(COD)_2NiLi_2(THF)_4$ crystallizes out in the form of red-yellow crystals, which are twice washed with ether and dried for one hour at 0° C. in an oil pump vacuum.

Yield: 67 g=80% of the theory with respect to the $(COD)_2Ni$ put in.

Calculated: Ni, 10.17%; Li, 2.4%. Found:Ni, 10.15%; Li, 2.45%.

EXAMPLE 3

The reaction of $(C_5H_5)_2Ni$ in THF in the presence of COD with excess lithium sand at 0° C. yields, after the separation of unreacted lithium, a solution of $(COD)_2NiLi_2(THF)_4$ in tetrahydrofuran.

EXAMPLE 4

3.2 g of $(COD)_2NiLi_2(THF)_4$ in 60 ml of THF is reacted with 1.1 g of $(C_5H_5)_2Ni$ in the presence of COD, at 0° C. The $(COD)_2Ni$ precipitates in the form of a light yellow precipitate which is washed with a little THF and dried in an oil pump vacuum.

Yield: 1.3 g=42% of the theory with respect to the $(C_5H_5)_2Ni$ put in.

Calculated: Ni, 21.3%. Found: Ni, 21.5%.

EXAMPLE 5

20 g of $(C_5H_5)_2Co$ in 200 ml of THF is stirred with excess lithium sand under argon at $-30°$ C. After 45 minutes, the unreacted lithium is filtered out with a glass frit. When the filtrate is chilled to $-78°$ C. (2 hours), crystallization of $(C_5H_5)_2CoLi(THF)_{2.5}$ occurs, which is filtered off at $-78°$ C. and washed twice with cold pentane ($-78°$ C.). The extremely air-sensitive compound is then dried in a high vacuum at $-30°$ C.

Yield: 28 g=72% of the theory with respect to the $(C_5H_5)_2Co$ put in.

Calculated: Co, 15.67%; Li, 1.84%. Found:Co, 15.9%; Li, 1.7%.

Without isolation, or using the product isolated at intervals, the procedure continues as follows:

Under argon, 5.1 g of $(C_5H_5)_2CoLi(THF)_{2.5}$ is suspended in 60 ml of pentane at $-30°$ C. and transferred to a steel autoclave. Then ethylene is injected to a pressure of 30 atmospheres and the autoclave is brought to room temperature. After 2 hours, the liquid is filtered at room temperature through a glass frit, and the residue is washed with a small amount of pentane. After the filtrate has been vaccum-concentrated to about 20 ml and chilled to $-78°$ C., $C_5H_5Co(C_2H_4)_2$ crystallizes out. The compound is filtered off and dried at room temperature in a current of argon.

Yield: 1.5 g=67% of the theory with respect to the CoLi compound in.

Calculated: Co, 32.75%. Found: Co, 31.1%.

EXAMPLE 6

To 41.4 g of $(C_5H_5)_2Co$ and 54 ml of COD in 250 ml of THF, a total of 1.53 g of lithium sand is added at 0° C. over a period of 6 hours. The reaction is allowed to continue for 12 hours at room temperature, and then the tetrahydrofuran is distilled off in vacuo. The solid residue is dissolved at room temperature in toluene. The $C_5H_5Li$ is filtered out and the filtrate is chilled to $-60°$ C., whereupon brown $C_5H_5CoCOD$ crystallizes out and is washed with pentane and dried at room temperature in an oil pump vacuum.

Yield: 40.8 g=80% of the theory with respect to $(C_5H_5)_2Co$ put in.

Calculated: Co, 25.4%. Found: Co, 24.3%.

EXAMPLE 7

An ethylene-saturated mixture of 10.4 g of $C_5H_5CoCOD$ and 150 ml of THF is stirred with excess lithium sand under ethylene (1 atmosphere) for 5 hours at $-30°$ C. The initially dark red solution has then become light yellow. Then, at room temperature, the excess lithium is filtered off and the filtrate is concentrated in an oil pump vacuum to an oil. Upon the addition of ethylene-saturated ether as well as tetramethylethylenediamine (TMED), light yellow $CODCo(C_2H_4)_2Li(TMED)_2$ precipitates in crystalline form; it is washed with a mixture of ether and TMED and dried at room temperature in an oil pump vacuum for one hour.

Yield: 14.5 g=70% of the theory with respect to $C_5H_5CoCOD$ put in.

Calculated: Co, 12.75%; Li, 1.5%. Found:Co, 12.4%; Li, 1.54%.

EXAMPLE 8

11.6 g of $C_5H_5CoCOD$ and 11 ml of all-trans-cyclododecatriene(1,5,9) $(C_{12}H_{18})$ in 200 ml of THF are stirred with excess lithium sand for six hours at $-30°$ C. The mixture is let stand for twelve hours at $-30°$ C. and then the tetrahydrofuran is distilled out in vacuo. The residue is dissolved with toluene and the $C_5H_5Li$ as well as the excess lithium is separated. 20 ml of tetramethylethylenediamine (TMED) is added to the filtrate and let stand for twelve hours at 0° c. Red $CODCoC_{12}H_{18}Li(TMED)_2$ crystallizes out, and is washed with ether and dried at room temperature in an oil pump vacuum.

Yield: 10.8 g=39% of the theory with respect to the $C_5H_5CoCOD$ put in.

Calculated: Co, 10.37%; Li, 1.22%. Found:Co, 10.24%; Li, 1.28%.

The filtrate separated from the $CODCoC_{12}H_{18}Li(TMED)_2$, after removal of the toluene with an oil pump vacuum, yields a red oil, which is stable at room temperature, and which consists substantially of isomeric $C_8H_{12}CoC_{12}H_{18}Li$ compounds.

EXAMPLE 9

As in Example 8, 14.8 g of $C_5H_5CoCOD$ in 200 ml of THF is stirred with 6.2 g of finely chopped potassium for ten hours under ethylene at $-30°$ C. Then the reaction mixture is held at $-78°$ C. for twelve hours, after which the $C_5H_5K$ and excess potassium are filtered out. After the filtrate has been concentrated by evaporation to about 50 ml and 200 ml of ether has been added, $CODCo(C_2H_4)_2K(THF)_1$ precipitates at room temperature in the form of a light yellow powder. The compound is washed with ether and dried in an oil pump vacuum at room temperature.

Yield: 14.4 g=68% of the theory with respect to $C_5H_5CoCOD$.

Calculated: Co, 17.64%; K, 11.70%. Found:Co, 17.0%; K, 11.6%.

EXAMPLE 10

To 60 g of $(C_5H_5)_2Co$ and 117 ml of COD in 500 ml of THF a total of 11 g of lithium sand is added, with stirring, at 0° C., over a period of six hours. After the withdrawal of the solvent, 500 ml of toluene is added to the residue and the mixture is stirred for one half hour at room temperature. The $C_5H_5Li$ as well as excess lithium metal are then separated and the filtrate is thoroughly concentrated in vacuo. Then 300 ml of THF is added, as well as 300 ml of diethyl ether. At 0° C., light yellow $(COD)_2CoLi(THF)_x$ crystallizes out, is removed by filtration, and is washed with pentane and dried at room temperature in an oil pump vacuum.

Yield: 110.8 g=82% of the theory with respect to $(C_5H_5)_2Co$.

$(COD)_2CoLi(THF)_x$ can be recrystallized as follows: 57 g of $(COD)_2CoLi(THF)_x$ is dissolved in 600 ml of diethyl ether at room temperature and a small amount of insoluble is filtered out. When the filtrate is chilled to −30° C., yellow $(COD)_2CoLi(THF)_2$ crystallizes out, is washed with pentane, and is dried at 0° C. in an oil pump vacuum.

Yield: 40 g=70% of the theory with respect to $(COD)_2CoLi(THF)_x$ put in.

Calculated: Co, 13.83%; Li, 1.63%. Found:Co, 13.8%; Li, 1.67%.

EXAMPLE 11

The reaction of $(C_5H_5)_2Co$ with excess sodium metal and COD in THF at 0° C. yields, after separation of unreacted sodium, a yellow solution of $(COD)_2CoNa$ in tetrahydrofuran.

EXAMPLE 12

Similarly to Example 11, 20 g of $(C_5H_5)_2Co$ and 40 ml of COD in 300 ml of THF are stirred for about ten hours at 0° C. with excess metallic potassium. Then the reaction mixture is cooled to −78° C. and let stand for twelve hours. After the separation of the $C_5H_5K$ and of the unreacted potassium at −78° C., the filtrate is concentrated by evaporation at room temperature to about 100 ml, and a large amount of ether is added. At −30° C., yellow $(COD)_2CoK(THF)_{0.5}$ crystallizes out over a period of three days. This is washed with diethyl ether and dried at room temperature in an oil pump vacuum.

Yield: 24 g=63% of the theory with respect to $(C_5H_5)_2Co$ put in.

Calculated: Co, 15.26%; K, 10.12% for $(COD)_2CoK(THF)_1$. Found: Co, 16.4%; K, 10.9%.

EXAMPLE 13

3.6 ml of methanol is added to 41 g of $(COD)_2CoLi(THF)_2$ in 400 ml of toluene at −10° C. The mixture is allowed to rise to room temperature and $CH_3OLi$ is filtered out. Then, the filtrate is concentrated in vacuo and chilled to −78° C. Dark $(C_8H_{12})(C_8H_{13})Co$ crystallizes out.

Yield: 17.1 g=65% of the theory with respect to the $(COD)_2CoLi(THF)_2$.

Calculated: Co, 21.35%. Found: Co, 20.8%.

7.1 g of $(C_8H_{12})(C_8H_{13})Co$ in 50 ml of THF is stirred for two hours at 0° C. with 540 mg of lithium. The now dark red reaction solution is filtered free of the unreacted lithium. The THF is partially removed by vacuum distillation, and then diethyl ether is added. At −30° C., dark red $(C_8H_{12})(C_8H_{13})CoLi_2(THF)_4$ crystallizes out and is washed with ether and dried at 0° C. in an oil pump vacuum.

Yield: 7.7 g=50% of the theory with respect to the $(C_8H_{12})(C_8H_{13})Co$ put in.

Calculated: Co, 10.2%; Li, 2.4%. Found:Co, 10.2%; Li, 2.45%.

EXAMPLE 14

50 g of $(C_5H_5)_2Fe$ and 100 ml of COD in 350 ml of THF are stirred with excess lithium sand for six hours at −40° to −50° C. Then, at −40° C., excess lithium is filtered out and the filtrate is concentrated in vacuo to 250 ml. 150 ml of tetremethylethylenediamine (TMED) and 600 ml of diethyl ether are added and the mixture is let stand for sixteen hours at room temperature. Yellow $C_5H_5FeCODLiTMED$ precipitates, which is washed with a total of 500 ml of diethyl ether and dried in an oil pump vacuum at room temperature.

Yield: 71.2 g=75% of the theory with respect to the $(C_5H_5)_2Fe$ put in.

Calculated: Fe, 15.85%; Li, 1.97%. Found:Fe, 15.4%; Li, 2.05%.

EXAMPLE 15

As in Example 14, 50 g of $(C_5H_5)_2Fe$ together with 75 ml of COD in 320 ml of dimethoxyethane (DME) is stirred with excess lithium sand for six hours at −35° C. The mixture is allowed to rise to room temperature and the lithium is filtered out. When the filtrate is chilled to −30° C. (40 hours), an orange colored product crystallizes out. This is filtered off at −30° C. and stirred for two hours at room temperature with 600 ml of diethyl ether. Yellow $C_5H_5FeCODLiDME$ is obtained, which is washed with 200 ml of diethyl ether and dried for one hour at 40° C. in an oil pump vacuum.

Yield: 57.5 g=65.5% of the theory with respect to the $(C_5H_5)_2Fe$ put in.

Calculated: Fe, 17.1%; Li, 2.13%. Found:Fe, 16.6%; Li, 2.3%.

EXAMPLE 16

$(C_2H_4)_4CoK(THF)_{0.5}$

An ethylene-saturated mixture of 11 g of $(C_5H_5)_2Co$ in 150 ml of THF is stirred for 6 hours with 9.4 g of finely chopeed potassium at −30° C. under ethylene (1 atmosphere of excess pressure). Then the mixture is allowed to rise to 0° C., allowed to continue to react for 5 hours at 0° C., and then chilled down to −78° C. After about 5 hours the excess potassium and precipitated $C_5H_5K$ are filtered out at −78° C., and the light yellow filtrate is concentrated in an oil pump vacuum down to about 50 ml. After the addition of 200 ml of ether, $(C_2H_4)_4CoK(THF)_x$ precipitates in the form of a virtually colorless powder. The extremely air-sensitive compound is washed with ether at room temperature and dried for 30 minutes at room temperature in an oil pump vacuum.

Yield: 11.2 g=80% of the theory with respect to $(C_5H_5)_2Co$.

Calculated: Co, 23.95%; K, 15.89% for $(C_2H_4)_4CoK(THF)_{0.5}$. Found:Co, 24.6%; K, 16.5%.

EXAMPLE 17

$(C_2H_4)_4FeLi_2(TMED)_2$

A mixture of 10 g of $(C_5H_5)_2Fe$ and 3 g of finely chopped lithium in 75 ml of THF is saturated with ethylene at −40° C. and then transferred to a steel autoclave. Ethylene is forced in to a pressure of 5 atmospheres gauge, the mixture is allowed to warm to room temperature with stirring, and stirring is continued, first for 20 minutes at room temperature, and then for 7 hours at +50° C. Throughout the entire reaction time an autoclave pressure of 3 to 5 atmospheres gauge is sustained by the repeated pumping in of ethylene. After the end of the reaction, the autoclave content is transferred under argon to a G-4 glass frit, separated from a small amount of insoluble by-products and from excess lithium, and the yellow-brown filtrate is treated with 80 ml of ether and with 50 ml of tetramethylenediamine (TMED). At 0° C., light yellow $(C_2H_4)_4FeLi(TMED)_2$ precipitates in crystalline form, is filtered off after three hours, is washed with ether, and is dried at room temperature in an oil pump vacuum.

Yield: 12.9 g=58% of the theory with respect to the $(C_5H_5)_2Fe$.

Calculated: Fe, 13.49%; Li, 3.35%. Found:Fe, 13.0%; Li, 3.5%.

What is claimed is:

1. Method of preparing transition metal-olefin complex compounds and alkali metal-transition metal-olefin complex compounds or their solutions, either containing $C_5H_5$ or free of $C_5H_5$, respectively, which essentially comprises reacting transition-metallocene complex compounds of metals of Group VIII or metals chromium, molybdenum, titanium or vanadium with an alkali metal or an alkali metal-transition metal complex compound, in suitable solvents, at temperatures between −60° C. and +100° C.

2. Method of claim 1, characterized in that the transition metals are iron, cobalt and nickel.

3. Method of claim 1, characterized in that chromium, molybdenum, titanium or vanadium are used instead of the transition metals of Group VIII.

4. Method of claim 1 characterized in that the reaction between the transition-metallocene complex compounds or metals of Group VIII or metals chromium, molybdenum, titanium or vanadium with an alkali metal or an alkali metal-transition metal complex compound is carried out in the presence of an olefin.